United States Patent [19]

Anderson

[11] 4,117,013

[45] Sep. 26, 1978

[54] CATALYSTS FOR THE AMMONOLYSIS OF PENTAERYTHRITYL TETRACHLORIDE

[75] Inventor: William S. Anderson, Sunnyvale, Calif.

[73] Assignee: United Technologies Corporation, Hartford, Conn.

[21] Appl. No.: 806,049

[22] Filed: Jun. 13, 1977

Related U.S. Application Data

[63] Continuation-in-part of Ser. No. 698,580, Jun. 23, 1976, abandoned.

[51] Int. Cl.$^2$ .............................................. C07C 85/04
[52] U.S. Cl. ................................ 260/585 A; 252/426; 252/429 R; 252/431 N; 260/270 R; 260/283 S; 260/289 R; 260/348.1; 260/567.5; 260/567.6 M; 260/570.8 R; 260/570.9; 260/583 R; 260/584 R; 260/611 A; 260/612 D; 260/348.48; 260/348.63
[58] Field of Search ............... 260/585 A, 581, 567.5, 260/567.6 M, 583 R, 611 A, 348 R; 252/426, 429 R, 431 N

[56] References Cited

U.S. PATENT DOCUMENTS

| B 490,946 | 2/1976 | Bechara et al. | 252/426 X |
|---|---|---|---|
| 3,389,179 | 6/1968 | James | 260/585 A |
| 3,399,236 | 8/1968 | Mills | 260/585 A |
| 3,422,145 | 1/1969 | Steinmetz | 260/585 A |
| 3,790,634 | 2/1974 | Weiss | 260/583 N |
| 3,882,181 | 5/1975 | Forster et al. | 260/583 N |
| 3,988,267 | 10/1976 | Bechara et al. | 252/426 X |

OTHER PUBLICATIONS

Govaert, "Proc. Acad. Sci. Amsterdam", vol. 37, pp. 156–162, (1934).

Alphen, "Rec. Trav. Chim.", vol. 57, pp. 265–276 (1938).

*Primary Examiner*—Winston A. Douglas
*Assistant Examiner*—John J. Doll
*Attorney, Agent, or Firm*—Steve F. Stone

[57] ABSTRACT

It has been found that the following materials act as catalysts for the conversion of PETC to PETA by the ammonolysis of PETC in methanolic ammonia: (a) amine acid addition salts and quaternary ammonium halides and hydroxides, (b) tertiary amines, (c) olefin epoxides, (d) 8-hydroxyquinolines, (e) amine phenoxides, (f) quaternary hydroxyalkyl ammonium hydroxides, and (g) glycidyl halides and ethers. The preferred catalysts, according to this invention, include tetramethyl ammonium chloride, benzyl dimethylamine, dodecyl dimethylamine and 1,2-epoxy decane.

23 Claims, No Drawings

CATALYSTS FOR THE AMMONOLYSIS OF PENTAERYTHRITYL TETRACHLORIDE

RELATED PATENT APPLICATION

This application is a continuation-in-part of co-pending, co-assigned patent application Ser. No. 698,580, William S. Anderson, Catalysts for the Ammonolysis of Pentaerythrityl Tetrachloride filed June 23, 1976, now abandoned.

BACKGROUND OF THE INVENTION

Pentaerythrityl tetramine (PETA) is an extremely useful material, having known utility in the synthesis of high melting spiro polyamides, the cure of epoxy resins, the isolation and purification of copper, rare earths and other metals and, in combination with air and other oxidizing agents as an etchant of iron, steel, stainless steel and copper. The only published method for synthesizing PETA of which the inventor is aware, is set forth in Litherland and Mann, Journal of The Chemical Society, 1938, page 1588. This procedure is laborious, time-consuming, expensive, hazardous and low-yielding.

Recently, a method for synthesizing PETA by the ammonolysis of the corresponding pentaerythrityl tetrachloride (PETC) at temperatures in the range of 160°–180° C and at pressures of 1000 psi and over in an excess of methanolic ammonia was developed. This process constituted a substantial improvement over the prior art teachings of Litherland and Mann; however, the yields were relatively low (10–30% of the theoretical yield) and even at the high pressures employed, the reaction proceeded at a much slower rate than would be desirable. According to my invention, I have discovered that certain materials act as catalysts for this ammonolysis reaction, substantially increasing the percentage of conversion and substantially decreasing the reaction time. Since the process must be carried out in high pressure equipment and the reactants are extremely corrosive even to the stainless steel normally used in this equipment, the shortening of the reaction time is advantageous for reasons other than the savings in processing time that are obtained.

It is, accordingly, an object of this invention to provide catalysts for the ammonolysis of PETC.

It is another object of this invention to provide a process for the preparation of PETA by the ammonolysis of PETC.

These and other objects of the invention will be readily apparent from the following description.

DESCRIPTION OF INVENTION

It has been found that the following materials act as catalysts for the conversion of PETC to PETA by the ammonolysis of PETC in methanolic ammonia:

(a) amine acid addition salts and quaternary ammonium halides and hydroxides, having the formula

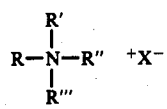

wherein R, R', and R" are hydrogen or alkyl groups containing 1-18 carbon atoms, R''' is selected from the group consisting of alkyl, hydroxyalkyl, aryl and aralkyl groups containing 1-18 carbon atoms and X is a halogen or hydroxide group;

(b) tertiary amines having the formula

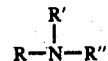

wherein R, R', and R" are alkyl, aryl, hydroxyalkyl and aralkyl groups containing from 1-18 carbon atoms, which tertiary amines are converted to the corresponding quaternary ammonium halide in the ammonolysis process;

(c) olefin epoxides having the formula

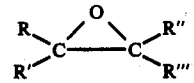

wherein R, R', R" and R''' are hydrogen, alkyl and aryl groups having from 1-18 carbon atoms and which epoxides react with ammonia or amines in the ammonolysis process;

(d) heterocyclic amines having the formula

which are converted to salts of an amine phenoxide in the ammonolysis process and wherein R and R' are hydrogen, halogen, sulfonic acid or alkyl groups containing from 1-18 carbon atoms and the metal and acid salts thereof;

(e) salts of an amine phenoxide of the formula

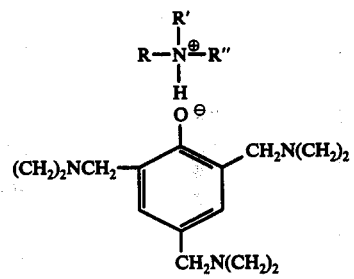

wherein R, R' and R" are hydrogen or alkyl groups containing from 1-18 carbon atoms;

(f) quaternary hydroxyalkyl ammonium hydroxides having the formula

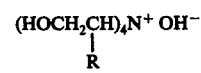

wherein R is hydrogen or an alkyl group having from 1-6 carbon atoms; and (g) glycidyl halides and ethers having 1-18 carbon atoms.

The preferred catalysts, according to this invention, include tetramethyl ammonium chloride, benzyl dimethylamine, dodecyl dimethylamine and 1,2-epoxy decane.

Representative compounds of each group include, without limitation:

(a) amine acid addition salts and quaternary ammonium halides and hydroxides: tetramethyl ammonium chloride, bromide or hydroxide tetraethyl ammonium chloride, bromide or hydroxide benzyl dimethyl decyl ammonium chloride, bromide or hydroxide, benzyl dimethyl ammonium chloride, bromide or hydroxide, cetyl trimethyl ammonium chloride, bromide or hydroxide, and choline chloride.

(b) tertiary amines: benzyl dimethyl amine dodecyl dimethyl amine trimethylamine tributylamine (c) olefin epoxides: 1,2-epoxy decane 1,2-epoxy butane 1,2-epoxy hexane styrene oxide (d) heterocyclic amines: 8-hydroxyquinoline 5-chloro-8-hydroxyquinoline 5,7-dichloro-8-hydroxyquinoline 8-hydroxyquinolin-5-sulfonic acid copper 8-quinolate 8-hydroxyquinoline citrate, sulfate or benzoate (e) salts of an amine phenoxides: ammonium salt of tri(dimethylaminomethyl)phenol (f) quaternary hydroxyalkyl ammonium hydroxides: tetraethanol ammonium hydroxide tetraisopropanol ammonium hydroxide (b) glycidyl halides and ethers: epichlorohydrin phenyl glycidyl ether cresyl glycidyl ether The amount of catalyst is not critical although the catalyst is preferably present in amounts from 0.1 to 5% of the reaction mixture. A greater or lesser amount can be employed so long as catalytic effect is observed. The reaction is preferably conducted at temperatures from 160°–180° C and at pressures of at least about 1000 psi.

In order to demonstrate the effect of catalysts of this invention on the reaction, the ammonolysis reaction was carried out in one-gallon Magnadash autoclave into which was charged 300 gms of PETC, 2 liters of methanol and sufficient ammonia as to enable the temperatures and pressures shown in the following table to be obtained. Typically, this amount of ammonia was from 400–1400 gms. The reaction was carried out using no catalyst as a control. The reaction times and yield of PETA are shown in Table I.

TABLE I

AMMONOLYSIS OF PENTAERYTHRITYL TETRACHLORIDE

| Catalyst and Grams | Reaction Time, Hrs. | Temp. °C | Pressure PSIG | Pentaerythrityl tetramine Yield (Gms. and % of Theoretical) |
|---|---|---|---|---|
| None | 5–10 | 174–176 | 3,000–5,000 | 19–57 (10–30%)[a] |
| 1,2-epoxy-decane, 5 g | 2.3 | 176–185 | 4,200–5,200 | 53 (30%) |
| Dodecyl dimethylamine, 5 g | 2.3 | 171–176 | 3,000–5,000 | 62 (39%) |
| Cetyl trimethyl ammonium chloride, 5 g | 2.0 | 174–178 | 3,800–5,600 | 37 (21%) |
| Tris (dimethylaminomethyl) phenol, 5 g | 2.0–2.5 | 175–183 | 3,000–5,000 | 40 (26%)[b] |
| Benzyl dimethyl amine, 5 g | 2.5 | 175–176 | 4,500–5,000 | 54 (46%) |
| Benzyl dimethyl amine, 5 g + decyl chloride, 6.7 g | 2.3 | 175–177 | 3,400–5,000 | 55 (49%) |
| Tetramethyl ammonium chloride, 5 g | 2.0 | 174–175 | 3,000–3,500 | 55 (57%) |
| Epichlorohydrin, 5 g | 3.0 | 174–175 | 3,900–4,400 | 0.4 (0.3%)[b] |
| Tetramethyl ammonium bromide, 5 g | 3.0 | 174–175 | 3,600–4,500 | 61 (43%)[c] |
| Tetramethyl ammonium chloride, 15 g | 2.5 | 171–174 | 3,800–4,500 | 56 (49%) |
| Tetraethyl ammonium chloride, 15 g | 3.0 | 175 | 3,800–4,500 | 55 (36%) |
| Hydroxyquinoline, 5 g | 3.0 | 174–175 | 3,500–4,500 | 48 (35%) |
| Tetraethanol ammonium hydroxide, 15 g | 2.3 | 173–175 | 3,500–4,500 | 40 (39%) |
| Phenyl glycidyl ether 15 g | 2.3 | 172–175 | 3,500–4,500 | 51 (34%) |

[a]Range of conditions and results from 10 runs.
[b]Agitation lost during this run.
[c]Heavy corrosion of reactor.

As can be seen, the reaction time needed to produce yields comparable to and greater than those obtained without the catalyst of this invention was reduced by the use of the catalysts.

While this invention has been decided with respect to specific embodiments thereof, it should not be considered as limited thereto. Various modifications will be apparent to workers skilled in the art which can be made without departing from the scope of this invention which is limited only by the following claims, wherein

I claim:

1. In a process for converting pentaerythrityl tetrachloride to pentaerythrityl tetramine by ammonolysis in methanolic ammonia, the improvement which comprises adding to the reaction mixture a catalytic amount of a material selected from the group consisting of:

(a) amine acid addition salts and quaternary ammonium halides and hydroxides, having the formula

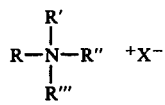

wherein R, R' and R" are selected from the group consisting of hydrogen and alkyl groups containing 1-18 carbon atoms, R'" is selected from the group consising of alkyl, hydroxyalkyl, aryl and aralkyl groups containing 1-18 carbon atoms and X is selected from the group consisting of halogen and hydroxide radicals;

(b) tertiary amines having the formula

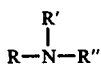

wherein R, R' and R" are alkyl, aryl, hydroxyalkyl and aralkyl groups containing from 1-18 carbon atoms, which tertiary amines are converted to the corresponding quaternary ammonium halide in the ammonolysis process;

(c) olefin epoxides having the formula

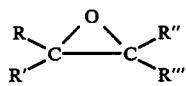

wherein R, R', R" and R'" are selected from the group consisting of hydrogen, alkyl and aryl groups having from 1-18 carbon atoms and which epoxides react with ammonia or amines in the ammonolysis process;

(d) heterocyclic amines having the formula

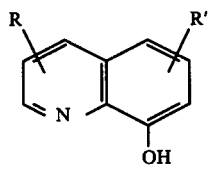

which are converted to amine phenoxide in the ammonolysis process and wherein R and R' are selected from the group consisting of hydrogen, halogen, sulfonic acid and alkyl groups containing from 1-18 carbon atoms, and the metal and acid salts thereof;

(e) salts of an amine phenoxide of the formula

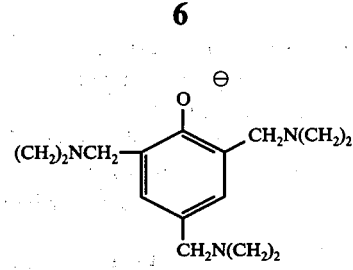

wherein R, R' and R" are hydrogen or alkyl groups containing from 1-18 carbon atoms:

(f) quaternary hydroxyalkyl ammonium hydroxides having the formula

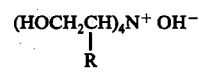

wherein R is selected from the group consisting of hydrogen and alkyl groups having from 1-6 carbon atoms; and (g) glycidyl halides and ethers having 1-18 carbon atoms.

2. The process of claim 1 wherein said material is selected from the group consisting of the quaternary ammonium halides and hydroxides defined by paragraph (a).

3. The process of claim 2 wherein said material is selected from the group consisting of tetramethyl ammonium chloride, tetramethyl ammonium bromide, tetramethyl ammonium hydroxide, tetraethyl ammonium chloride, tetraethyl ammonium bromide, tetraethyl ammonium hydroxide, benzyl dimethyl decyl ammonium chloride, benzyl dimethyl decyl ammonium bromide, benzyl dimethyl decyl ammonium hydroxide, cetyl trimethyl ammonium chloride, cetyl trimethyl ammonium bromide, cetyl trimethyl ammonium hydroxide, benzyl dimethyl ammonium hydroxide, benzyl dimethyl ammonium chloride, benzyl dimethyl ammonium bromide and choline chloride.

4. The process of claim 3 wherein said material is cetyl trimethyl ammonium chloride.

5. The process of claim 3 wherein said material is tetramethyl ammonium chloride.

6. The process of claim 3 wherein said material is tetraethyl ammonium chloride.

7. The process of claim 1 wherein said material is selected from the group consisting of the tertiary amines defined by paragraph (b).

8. The process of claim 7 wherein said material is selected from the group consisting of benzyl dimethyl amine, dodecyl dimethyl amine, trimethylamine and tributylamine.

9. The process of claim 8 wherein said material is benzyl dimethyl amine.

10. The process of claim 8 wherein said material is dodecyl dimethyl amine.

11. The process of claim 1 wherein said material is selected from the group consisting of the olefin epoxides defined by paragraph (c).

12. The process of claim 11 wherein said material is selected from the group consisting of 1,2-epoxy decane, 1,2-epoxy butane, 1,2-epoxy hexane and styrene oxide.

13. The process of claim 1 wherein said material is selected from the group consisting of the heterocyclic amines defined in paragraph (d).

14. The process of claim 13 wherein said material is selected from the group consisting of 8-hydroxyquinoline, 5-chloro-8-hydroxyquinoline, 5,7-dichloro-8-hydroxyquinoline, 8-hydroxyquinoline-5-sulfonic acid, copper 8-quinolate, 8-hydroxyquinoline citrate, 8-hydroxyqinoline sulfate and 8-hydroxyquinoline benzoate.

15. The process of claim 14 wherein said material is 8-hydroxyquinoline.

16. The process of claim 1 wherein said material is selected from the group consisting of the salts of amine phenoxides defined in paragraph (e).

17. The process of claim 16 wherein said material is tris (dimethylaminomethyl) phenol.

18. The process of claim 1 wherein said material is selected from the group consisting of the quaternary hydroxyalkyl ammonium hydroxides defined in paragraph (f).

19. The process of claim 18 wherein said material is tetraethanol ammonium hydroxide.

20. The process of claim 18 wherein said material is tetraisopropanol ammonium hydroxide.

21. The process of claim 1 wherein said material is selected from the group consisting of the glycidyl halides and ethers defined in paragraph (g).

22. The process of claim 21 wherein said material is epichlorohydrin.

23. The process of claim 21 wherein said material is phenyl glycidyl ether.

* * * * *